(12) United States Patent
Maarek

(10) Patent No.: US 9,668,701 B2
(45) Date of Patent: *Jun. 6, 2017

(54) DETECTION OF INSULIN RESISTANCE, DIABETES, CARDIOVASCULAR DISEASE AND AUTONOMIC NEUROPATHY

(71) Applicant: Medical Screening Corporation, Miami, FL (US)

(72) Inventor: Albert Maarek, Miami, FL (US)

(73) Assignee: Medical Screening Corporation, Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/075,923

(22) Filed: Mar. 21, 2016

(65) Prior Publication Data

US 2016/0345912 A1 Dec. 1, 2016

Related U.S. Application Data

(63) Continuation-in-part of application No. 14/717,276, filed on May 20, 2015, which is a continuation-in-part of application No. PCT/IB2013/002595, filed on Nov. 21, 2013.

(60) Provisional application No. 61/728,848, filed on Nov. 21, 2012.

(51) Int. Cl.
| | |
|---|---|
| *A61B 5/02* | (2006.01) |
| *A61B 5/00* | (2006.01) |
| *A61B 5/053* | (2006.01) |
| *A61B 5/024* | (2006.01) |
| *A61B 5/1455* | (2006.01) |
| *A61B 5/145* | (2006.01) |

(52) U.S. Cl.
CPC ........ *A61B 5/7275* (2013.01); *A61B 5/02416* (2013.01); *A61B 5/0533* (2013.01); *A61B 5/7257* (2013.01); *A61B 5/0022* (2013.01); *A61B 5/14532* (2013.01); *A61B 5/14552* (2013.01); *A61B 5/7239* (2013.01); *A61B 5/7246* (2013.01)

(58) Field of Classification Search
USPC .................................. 600/300, 324
See application file for complete search history.

(56) References Cited

U.S. PATENT DOCUMENTS

| | | | |
|---|---|---|---|
| 2007/0225606 A1* | 9/2007 | Naghavi | A61B 5/015 600/438 |
| 2013/0204103 A1* | 8/2013 | Maarek | A61B 5/0531 600/323 |

\* cited by examiner

*Primary Examiner* — Nicole F Johnson
*Assistant Examiner* — Nicole F. Lavert
(74) *Attorney, Agent, or Firm* — Mark Terry

(57) ABSTRACT

A method and system for detecting insulin resistance, diabetes, cardiovascular disease and/or autonomic neuropathy in a patient is provided. The method includes measuring a photoplethysmogram (PTG) and galvanic skin response from the patient, executing a spectral analysis on the PTG, comparing values derived from the PTG and the galvanic skin response of the patient to stored clinical data, calculating a PTG cardiovascular risk score based on the comparison, comparing further derived values to predefined values that correspond to certain diseases, including insulin resistance, diabetes, cardiovascular disease and autonomic neuropathy, and displaying the PTG cardiovascular risk score and said certain diseases that correspond to said predefined values.

20 Claims, 7 Drawing Sheets

| Area under the ROC curve (AUC) | 0.950 |
|---|---|
| Standard Error (a) | 0.0426 |
| 95% Confidence interval (b) | 0.803 to 0.996 |
| z statistic | 10.555 |
| Significance level P ( Area=0.5) | < 0.0001 |

(a) Hanley & McNeil, 1982
(b) Binomial exact

– 1 –

DETECTION OF INSULIN RESISTANCE, DIABETES, CARDIOVASCULAR DISEASE AND AUTONOMIC NEUROPATHY

CROSS-REFERENCE TO RELATED APPLICATIONS

This patent application is a continuation in part of patent application Ser. No. 14/717,276, filed May 20, 2015, and entitled "Method and Apparatus for Detection of Insulin Resistance, Diabetes and Cardiovascular Disease," which is a continuation in part of, and claims priority to, international application number PCT/IB2013/002595, filed Nov. 21, 2013, and entitled "Method and Apparatus for Detection of Insulin Resistance, Diabetes and Cardiovascular Disease," which claims priority to provisional patent application No. 61/728,848, filed on Nov. 21, 2012. The subject matter of patent application Ser. No. 14/717,276, PCT/IB2013/002595 and 61/728,848 are hereby incorporated by reference in their entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The technical field relates generally to the field of healthcare and, more specifically, relates to the field of diagnostic tests used for diagnosing various maladies.

BACKGROUND

Diabetes, cardiovascular disease and autonomic neuropathy have become epidemics in the United States. Tens of millions of Americans live with diabetes, cardiovascular disease and autonomic neuropathy. A majority of these individuals have been living with these afflictions for multiple numbers of years. The loss of productivity and daily activity due to these diseases is substantial. Additionally, it has been estimated that millions of individuals see a physician for treatment of these maladies every year. Additional millions will develop diabetes, cardiovascular disease and autonomic neuropathy in the near future. Thus, our healthcare system is significantly affected by the amount of resources that are allocated to treat diabetes, cardiovascular disease and autonomic neuropathy each year.

The prevalence of type 2 diabetes mellitus (T2DM) has increased in recent decades to epidemic proportions. About 150 million individuals worldwide had T2DM in 2000, and this number is expected to increase to—300 million by the year 2025. Because of the chronic course of T2DM and the significant morbidity and mortality associated with the vascular complications of the disease, T2DM has become not only a serious public health threat, but also a heavy economic burden on the health care system. The total annual cost of diabetes care in the United States was estimated to be $175 billion in the year 2007, and this number is expected to increase further with the increasing incidence of the disease.

The association of obesity with T2DM has been recognized for decades, and the major basis for this link is the ability of obesity to engender insulin resistance. Insulin resistance is a fundamental aspect of the etiology of T2DM and is also linked to a wide array of other pathophysiologic sequelae including hypertension, hyperlipidemia, atherosclerosis (i.e., the metabolic syndrome, or syndrome X), and polycystic ovarian disease. Insulin resistance carried a greater risk for developing cardiovascular disease than smoking or age or total/HDL cholesterol ratio. There are also grounds for considering the related possibility that insulin resistance and hyperinsulinemia, in addition to being caused by obesity, can contribute to the development of obesity.

Type 2 diabetes can progress undetected for many years, causing cardiovascular diseases. By the time patients are diagnosed with diabetes, up to 50% of them have cardiovascular complications. Recent studies indicate that early detection of diabetes cardiovascular complications can decrease diabetic mortality. However, the early detection of cardiovascular diseases is made difficult because symptoms are very often absent in patients. Thus, the detection of insulin resistance, diabetes and cardiovascular complications could be useful in diabetes treatment management and early detection of its complications.

The diagnosis of insulin resistance requires performing of the gold standard hyperinsulinemic euglycemic clamp (HE Clamp) which is costly, time consuming and inconvenient in routine clinical setting. The diagnosis of diabetes uses the blood tests such as Fasting Plasma Glucose (FPG) and Oral Glucose Tolerance Tests (OGTT). Studies demonstrate that FPG has a very low sensitivity to detect Diabetes and OGTT is costly and time consuming (exam duration is from 2 to 5 hours). Similarly, the diagnosis of cardiovascular diseases uses EKG, Stress Testing, Echocardiography, Chest X ray, EBCT and other Coronary Angiography. Also, the diagnosis of autonomic neuropathy uses a battery of tests including Ewing tests, heart rate variability analysis, sudomotor function, Nerve conductance study, thermal stimulation and other skin biopsy. There is no gold standard for said tests and the available battery of tests is costly and time consuming.

Therefore, in general, treatment for diabetes, cardiovascular disease and autonomic neuropathy can be more effective if these diseases are diagnosed accurately and early. Currently, however, the approaches available for diagnosing these maladies can be costly, time-consuming, inaccurate and imprecise. Further, there is no diagnostic process for these diseases that takes multitudes of factors into account, such as metadata of sensor readings from the patient. Another problem associated with the detection of said diseases is the lack of a generally-accepted paradigm for diagnosing diabetes, cardiovascular disease and autonomic neuropathy precisely. In the medical field, this leads to a great disparity in how diabetes, cardiovascular disease and autonomic neuropathy are diagnosed, charged and conducted.

Therefore, what is needed is a system and method for improving upon the problems with the prior art, and more particularly for a more efficient and precise way of diagnosing diabetes, cardiovascular disease and autonomic neuropathy.

SUMMARY

A method and system for detecting insulin resistance, diabetes, cardiovascular disease and/or autonomic neuropathy in a patient is provided. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, the method and system include the following steps: measuring a photoplethysmogram (PTG) and galvanic skin response from the patient; executing a spectral analysis on the PTG using Fast Fourier Transform, thereby generating three constituent frequencies: PTG high frequency (PTGHF), PTG low frequency (PTGLF) and PTG very low frequency (PTGVLF) based on the PTG; calculating PTG Total Power (PTGTP) as the sum of PTGHF, PTGLF, and PTGVLF; calculating PTG index (PTGi) of the spectral analysis as a sum of amplitudes of the PTGHF, PTGLF, and PTGVLF; calculating PTG VLF index (PTGVLFi) of the spectral analysis as PTGVLF divided by a value derived from the galvanic skin response; calculating PTG ratio (PTGr) of the spectral analysis as PTGVLF divided by PTGi; comparing the PTGi, PTGVLFi, and PTGr of the patient to stored clinical data; calculating a PTG cardiovascular risk score based on the comparison of the PTGi, PTGVLFi, and PTGr of the patient to the stored clinical data; and comparing PTGTP, PTGi and PTGVLFi to predefined values that correspond to certain diseases, including insulin resistance, diabetes, cardiovascular disease and autonomic neuropathy; and displaying the PTG cardiovascular risk score and said certain diseases that correspond to predefined values that match the PTGTP and PTGi and PTGVLFi.

BRIEF DESCRIPTION OF THE DRAWINGS

The accompanying drawings, which are incorporated in and constitute a part of this disclosure, illustrate various example embodiments. In the drawings.

DETAILED DESCRIPTION

Figure 1:
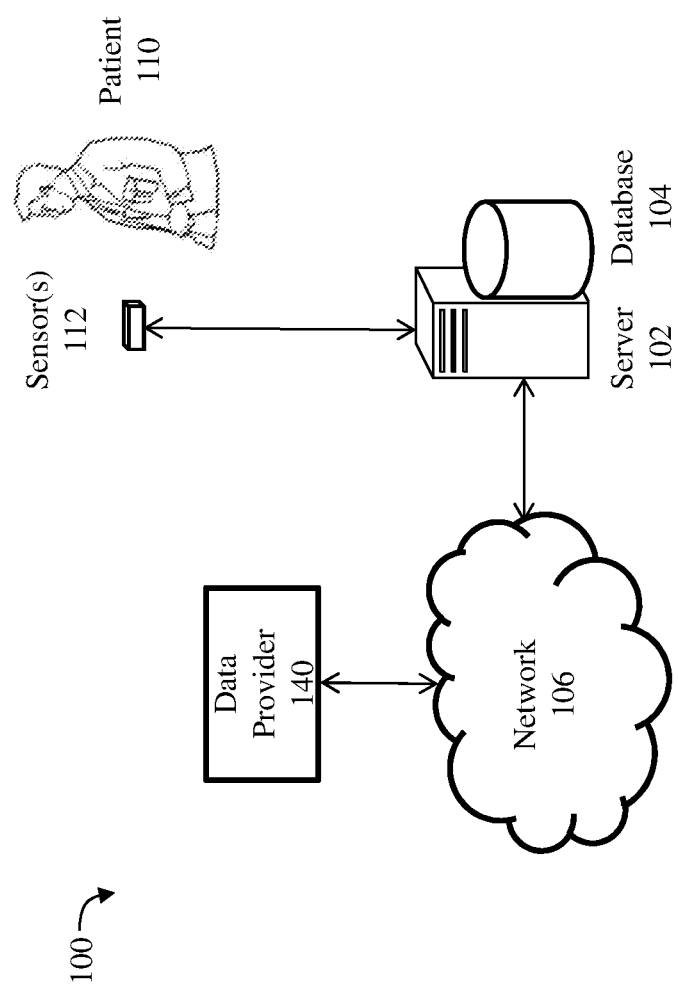
FIG. 1 is a block diagram of an operating environment that supports a method and system for detecting insulin resistance, diabetes, cardiovascular disease and/or autonomic neuropathy in a patient, according to an example embodiment.

The following detailed description refers to the accompanying drawings. Wherever possible, the same reference numbers are used in the drawings and the following description to refer to the same or similar elements. While embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the claimed subject matter. Instead, the proper scope of the claimed subject matter is defined by the appended claims.

The claimed subject matter improves upon the problems with the prior art by providing a system and method for allowing a physician or other healthcare professional to accurately detect insulin resistance, diabetes, cardiovascular disease and/or autonomic neuropathy in a patient in a timely and economically feasible manner. Further, the claimed subject matter provides a precise and automated way to diagnose insulin resistance, diabetes, cardiovascular disease and/or autonomic neuropathy in a patient, wherein the process takes multitudes of factors into account, such as various metadata collected from the patient. Also, the claimed subject matter provides a standardized paradigm for diagnosing insulin resistance, diabetes, cardiovascular disease and/or autonomic neuropathy in a patient. Further, the claimed subject matter allows for early detection of insulin resistance, diabetes, cardiovascular disease and/or autonomic neuropathy in a patient using a test that is convenient to execute in a routine clinical setting.

FIG. 1 is a block diagram of an operating environment 100 that supports a method and system for detecting insulin resistance, diabetes, cardiovascular disease and/or autonomic neuropathy in a patient, according to an example embodiment. The environment 100 may comprise at least two computing devices 140, 112 and a server 102, which may communicate via a communications network 106. The computing devices 140, 112, 102 may be connected either wirelessly or in a wired or fiber optic form to the communications network 106. The at least one sensor 112 may be communicatively coupled, either wirelessly or in a wired or fiber optic form to the server 102. Communications network 106 may be a packet switched network, such as the Internet, or any local area network, wide area network, enterprise private network, cellular network, phone network, mobile communications network, or any combination of the above.

Sensor 112 and computing devices 140, 102 may each comprise a computing device 600, described below in greater detail with respect to FIG. 6. In one embodiment, at least one sensor 112 may be a pulse oximeter, and/or galvanic skin response device that records data from a patient 110. In another embodiment, at least one sensor 112 may include functions that record other vital information of patient 110, such as blood pressure, heart rate, wattage output, pulse oximetry, skin conductance, breathing rate. Further, sensor 112 and computing devices 140, 102 may each comprise mobile computing devices such as cellular telephones, smart phones, tablet computers, wearable devices, or other computing devices such as a desktop computer, laptop, game console, etc. In one embodiment, the at least one sensor 112 may be integrated with computing device 102.

Server 102 includes a software engine that delivers applications, data, program code and other information to networked devices 112, 140. The software engine of server 102 may perform other processes such as transferring multimedia data, such as audio and video, in a stream of packets that are interpreted and rendered by a software application as the packets arrive. It should be noted that although FIG. 1 shows only a certain number of computing devices, the disclosed system supports any number of computing devices that may be connected via network 106.

Server 102, and computing devices 112, 140 may each include program logic comprising computer source code, scripting language code or interpreted language code that perform various functions. In one embodiment, the aforementioned program logic may comprise program module 607 in FIG. 6.

FIG. 1 further shows that server 102 includes a database or repository 104, which may be a relational database comprising a Structured Query Language (SQL) database stored in a SQL server. Computing devices 112, 140 may also each include databases. The database 104 may serve data used by server 102, computing devices 112, 140 during the course of operation of the disclosed systems and methods.

Environment 100 may be used when the disclosed computing devices transfer data to and from database 104 coupled to server 102. Various types of data may be stored in the database 104 of server 102. For example, the database 104 may store one or more patient records for each patient, i.e., a patient record. A patient record may include personal data for the patient 110, which may include contact information for a patient 110, a medical history of the patient, demographic data of the patient, clinical data of the patient, and psychological data of the patient and occupational data of the patient. A patient record may also include assessment data for the patient, wherein the assessment data includes medical assessment data of the patient, functional assessment data of the patient, psychological assessment data of the patient and economic assessment data of the patient, or the like. A patient record may also include risk data based on the personal data for the patient 110, wherein the risk data defines the patient's risk of further developing a current affliction or having a recurrence of the current affliction, and result data based on the assessment data for the patient, wherein the result data defines a result of the exercise regimen in treating the current affliction.

Note that although server 102 is shown as a single and independent entity, in one embodiment, the functions of server 102 may be integrated with another entity, such as the computing device 112, 140. Further, server 102 and its functionality, according to a preferred embodiment, can be realized in a centralized fashion in one computer system or in a distributed fashion wherein different elements are spread across several interconnected computer systems.

Figure 2:
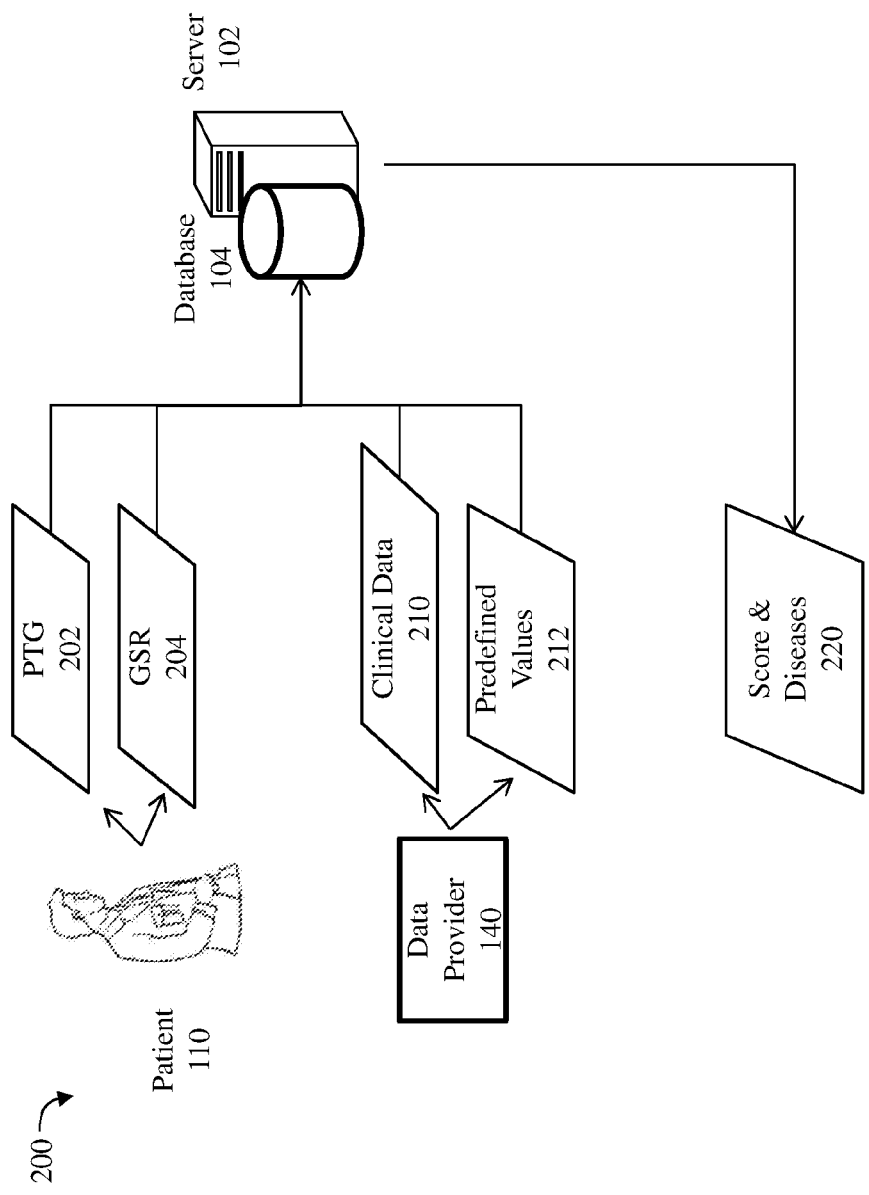
FIG. 2 is a diagram showing the data flow of the method and system for detecting insulin resistance, diabetes, cardiovascular disease and/or autonomic neuropathy in a patient, according to an example embodiment.
Figure 3:
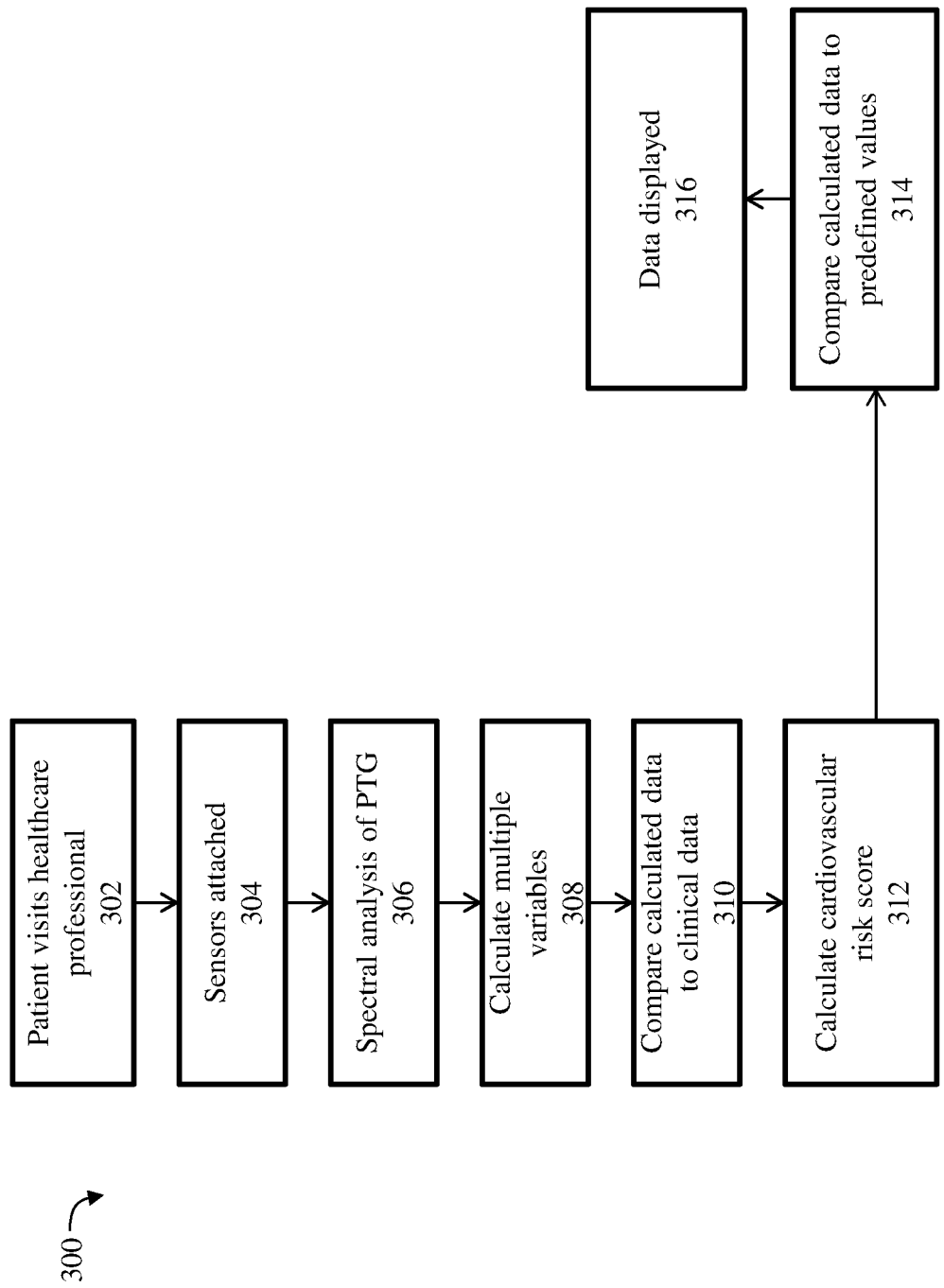
FIG. 3 is a flow chart of a method for detecting insulin resistance, diabetes, cardiovascular disease and/or autonomic neuropathy in a patient, according to an example embodiment.

FIG. 3 is a flow chart of a method 300 for detecting insulin resistance, diabetes, cardiovascular disease and/or autonomic neuropathy in a patient, according to an example embodiment. Method 300 describes the steps that occur when a patient 110 undergoes diagnosis by a healthcare professional for an affliction, such as insulin resistance, diabetes, cardiovascular disease and/or autonomic neuropathy, wherein the diagnosis process is facilitated by the use of environment 100. The method 300 is described with reference to FIG. 2, which is a diagram 200 showing the data flow of the process for facilitating treatment of patients, according to an example embodiment.

In an optional preliminary step, the method 300 begins with the database 104 receiving (such as via network 106) and storing clinical data 210 and predefined values 212 from, for example, a data provider 140, which may be a third party provider of data. Clinical data 210 refers to data that may be garnered from a clinical experiment or study that establishes parameters, ranges and/or normal values that are then used as a benchmark to measure other tested subjects. The clinical data may refer to clinical values or ranges for the variables PTGi, PTGVLFi, and PTGr (defined in greater detail below) from a tested group. In one alternative, clinical data 210 may also represent one or more ranges of values for one variable or attribute. For example, clinical data for PTGi may indicate a range of values from 20-33. In another alternative, clinical data 210 may also represent multiple ranges of values. For example, clinical data for PTGi may indicate a first range of values from 20-25, which indicates a normal range; a second range of values from 25-31, which indicates a borderline range; and a third range of values from 31 and above, which indicates an abnormal range.

Predefined values 212 may refer to predefined values (for variables PTGTP, PTGi and PTGVLFi—defined in greater detail below) that, according to research or empirical data, correspond to certain diseases, including insulin resistance, diabetes, cardiovascular disease and autonomic neuropathy. Thus, a given value of 33 for PTGTP, for example, may correspond to diabetes.

The method 300 begins in earnest with the first step 302 wherein a patient 110 may visit a healthcare professional or doctor. During the visit, which may be a conventional, in-person visit or a virtual visit using teleconferencing technology, the doctor, and/or another healthcare professional working under the direction of the doctor, may interact with the patient 110 in order to evaluate the patient medically and establish a diagnosis.

The healthcare professional may attach the at least one sensor 112 to the patient and during the visit, in step 304, certain information is generated and entered into the database 104 of server 102 as a patient record associated with patient 110. Said information may include a photoplethysmogram (PTG) 202 (garnered by a pulse oximeter) and galvanic skin response data 204 (garnered by a galvanic skin response device). A photoplethysmogram (PTG) is an optically obtained plethysmogram, a volumetric measurement of an organ. A PTG is often obtained by using a pulse oximeter which illuminates the skin and measures changes in light absorption. Galvanic skin response is the property of the human body that causes continuous variation in the electrical characteristics of the skin. Galvanic skin response is measured by a galvanic skin response sensor or device that measures the electrical conductance (or skin resistance) of the skin. Galvanic skin response may be represented by a value measured in micro Siemens, for example.

In step 306, device 102 executes a spectral analysis on the PTG using Fast Fourier Transform (FFT), thereby generating three constituent frequencies: PTG high frequency (PTGHF), PTG low frequency (PTGLF) and PTG very low frequency (PTGVLF) based on the PTG. A fast Fourier transform (FFT) algorithm computes the discrete Fourier transform (DFT) of a sequence, or its inverse. Fourier analysis converts a signal from its original domain (often time or space) to a representation in the frequency domain and vice versa. Specifically, in this scenario, the FFT transforms the PTG of 202 into three constituent frequencies, the high frequency, low frequency and very low frequency. The PTGHF may be a band between 0.15 and 0.6 Hz, the PTGLF may be a band ranging from 0.04 to 0.15 Hz, and the PTGVLF may be a band lower than 0.04 Hz. The FFT may use as a reference the heart rate with frequency values fixed at 1 Hertz at heart rate 60 bpm. Note that three constituent frequencies generated in this step also comprise amplitudes, which are used later in the method 300.

In step 308, the device 102 calculates PTG Total Power (PTGTP) as the sum of PTGHF, PTGLF, and PTGVLF. In one embodiment, the FFT may be performed on the first derivative of total record of the PTG trace and calculate PTGTP in milliseconds squared.

Further, the device 102 calculates PTG index (PTGi) of the spectral analysis as a sum of amplitudes of the PTGHF, PTGLF, and PTGVLF. Also, the device 102 calculates PTG VLF index (PTGVLFi) of the spectral analysis as PTGVLF divided by a value representing the galvanic skin response, measured in micro Siemens, for example. Finally, in this step, the device 102 calculates PTG ratio (PTGr) of the spectral analysis as PTGVLF divided by PTGi.

Next, in step 310, the device 102 compares the PTGi, PTGVLFi, and PTGr of the patient (calculated above) to stored clinical data 210. The comparison of this step results in data being stored, wherein said data represents the results of the comparison. For example, a PTGi value of 23 is compared to a clinical data 210, which shows a PTGi value of 33. Thus, in this example, the method 300 stores a data structure, or a numerical value (such as −1), that indicates that the generated PTGi value of 23 is less than the clinical PTGi value of 33. If the generated PTGi value was 33, the method 300 may store a data structure, or a numerical value (such as 0), that indicates that the generated PTGi value of 33 is equal to the clinical PTGi value of 33. If the generated PTGi value was 36, the method 300 may store a data structure, or a numerical value (such as +1), that indicates that the generated PTGi value of 33 is greater than the clinical PTGi value of 33.

In another example, clinical data for PTGi may indicate a range of values from 20-33. Thus, in this example, the method 300 stores a data structure, or a numerical value (such as −1) that indicates that a generated PTGi value of 19 is less than the clinical PTGi range of values. If the generated PTGi value was 25, the method 300 may store a data structure, or a numerical value (such as 0), that indicates that the generated PTGi value of 25 is within the clinical PTGi range of values. If the generated PTGi value was 35, the method 300 may store a data structure, or a numerical value (such as +1), that indicates that the generated PTGi value of 35 is greater than the clinical PTGi range of values.

In another example, clinical data 210 may also represent multiple ranges of values, wherein each range is associated with a superlative or degree. For example, clinical data for PTGi may indicate a first range of values from 20-25, which indicates a normal range; a second range of values from 26-31, which indicates a borderline range; and a third range of values from 32 and above, which indicates an abnormal range. Thus, in this example, the method 300 stores a data structure, or a numerical value (such as 0) that indicates that a generated PTGi value of 22 is within the clinical PTGi range of values of the normal range. If the generated PTGi value was 26, the method 300 may store a data structure, or a numerical value (such as 1), that indicates that the generated PTGi value of 26 is within the clinical PTGi range of values of the borderline range. If the generated PTGi value was 35, the method 300 may store a data structure, or a numerical value (such as 2), that indicates that the generated PTGi value of 35 is within the clinical PTGi range of values for the abnormal range.

In the later example above, the device 102 stores all numerical values that resulted from the comparison of the PTGi, PTGVLFi, and PTGr of the patient (calculated above) to stored clinical data 210. Also, device 102 may sum the numerical values garnered from the comparison of each of the values for PTGi, PTGVLFi, and PTGr to clinical data.

In step 312, the device 102, calculates a PTG cardiovascular risk score based on the comparison of the PTGi, PTGVLFi, and PTGr of the patient to the stored clinical data. Following is an example formula used to calculate the PTG cardiovascular risk score based on the comparison of the PTGi, PTGVLFi, and PTGr of the patient to the stored clinical data: calculate the sum of the numerical values garnered from the comparison of each of the values for PTGi, PTGVLFi, and PTGr to clinical data in step 310 above.

The PTG cardiovascular risk score may also be associated with one of more range of values. For example, a range of values from 0-1 may be considered normal. Thus, in this example, a PTG cardiovascular risk score of 1 indicates that the score is normal. In another example, the PTG cardiovascular risk score may also be associated with multiple ranges of values, wherein each range is associated with a superlative or degree. For example, a first range of values from 0-1 indicates a normal range; a second range of values from 2-3 indicates a borderline range; and a third range of values from 4 and above indicates an abnormal range. Thus, in this example, a numerical value of 5 indicates an abnormal value for the score.

Next in step 314, device 102 compares PTGTP, PTGi and PTGVLFi to predefined values 212 that correspond to certain diseases, including insulin resistance, diabetes, cardiovascular disease and autonomic neuropathy, and may also correspond to risk of certain diseases. In one embodiment, certain predefined values correspond directly to a particular disease, and may also correspond to risk of certain diseases. For example, a predefined value of 50 for PTGVLFi corresponds to diabetes with a high risk of autonomic neuropathy.

In another embodiment of the comparison of step 314, certain predefined values 212 are used as borderline numbers to separate normal or acceptable values from abnormal values that may correspond to a particular disease, and may also correspond to risk of certain diseases. For example, a predefined value of 33 is used to indicate that any number equal to or greater than 33 for PTGVLFi corresponds to diabetes with a high risk of autonomic neuropathy, while any number below 33 is a normal number not associated with a disease or a risk. A measurement of PTGTP greater than 370 ms$^2$, for example, suggests the patient has insulin resistance. A measurement of PTGi lower than 40, for example, suggests the patient has diabetes with high risk of cardiovascular disease. A measurement of PTGVLFi greater than 33, for example, suggests the patient has diabetes with a high risk of autonomic neuropathy. Thus, a predefined value (such as 33) for PTGVLFi corresponds to a particular disease.

In another embodiment of the comparison step 314, multiple ranges of values 212 may be used to show a correspondence to a particular disease, and may also correspond to risk of certain diseases. For example, for PTGi, a first range of values from 20-25 may indicate a normal range; a second range of values from 26-31, may indicate a borderline range; and a third range of values from 32 and above may indicate an abnormal range that corresponds to diabetes.

Finally, in step 316, device 102 displays the PTG cardiovascular risk score and said certain diseases (see item 220 in FIG. 2) that correspond to predefined values that match the PTGTP and PTGi and PTGVLFi. Alternatively, device 102 transmits the data over the network 106 to another computing device for storage and/or display on said other device.

Experimental Data

The claimed subject matter is supported by various clinical trials as described in the specific examples below. The experimental data supports the following conclusions. The correlation of M-value and PTGTP using the Spearman's coefficient was −0.624 (P.0.001). PTGTP had a sensitivity and specificity of 90% (cutoff 370 ms$^2$) to detect M-value <4.5 (P.0.0001). PTGi had a sensitivity of 86.1% and specificity of 87.3% (cutoff <40.8) to detect atherosclerosis (P.0.0001). Area under the Roc curve (AUC)=0.926. The correlations between PTGVLFi and cardiac autonomic neuropathy (CAN) score were r=0.64 (P.0.0001). The PTGi had a sensitivity of 92% and specificity of 80% (cut-off score >35.5) with the area under the curve=0.92) to detect diabetes. The PTGVLFi had a sensitivity of 92% and specificity of 87% (cut-off score >25.5) with the area under the curve=0.91 to detect diabetes. The correlations between the OGTT and PTGi were: r=−0.56 (p=0.003) for glucose, r=−0.41 (p=0.04) for insulin, and r=−0.50 (p=0.01) for insulin C-peptide.

Figure 4A:
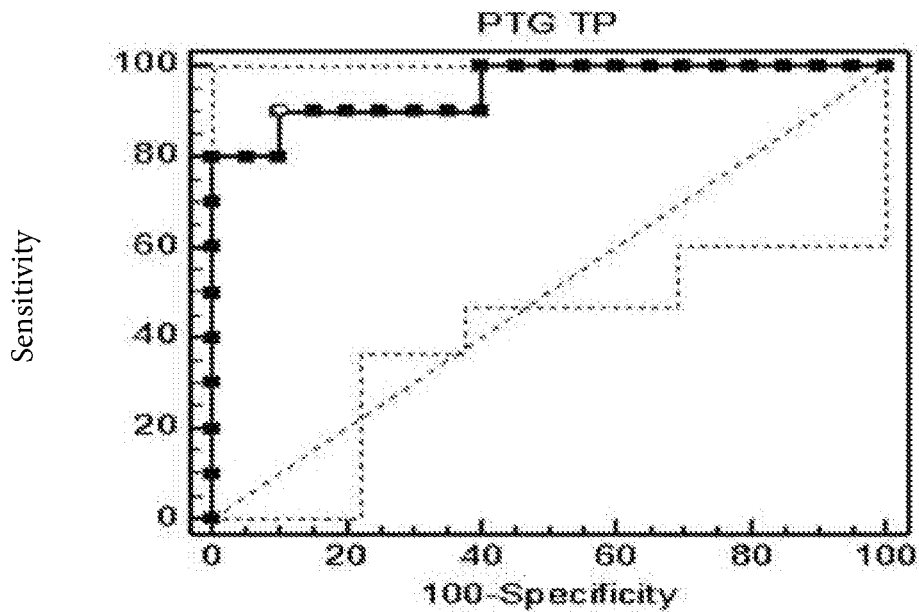
FIGS. 4A, 4B and 5 are graphs showing values for various variables, according to an example embodiment.
Figure 4B:
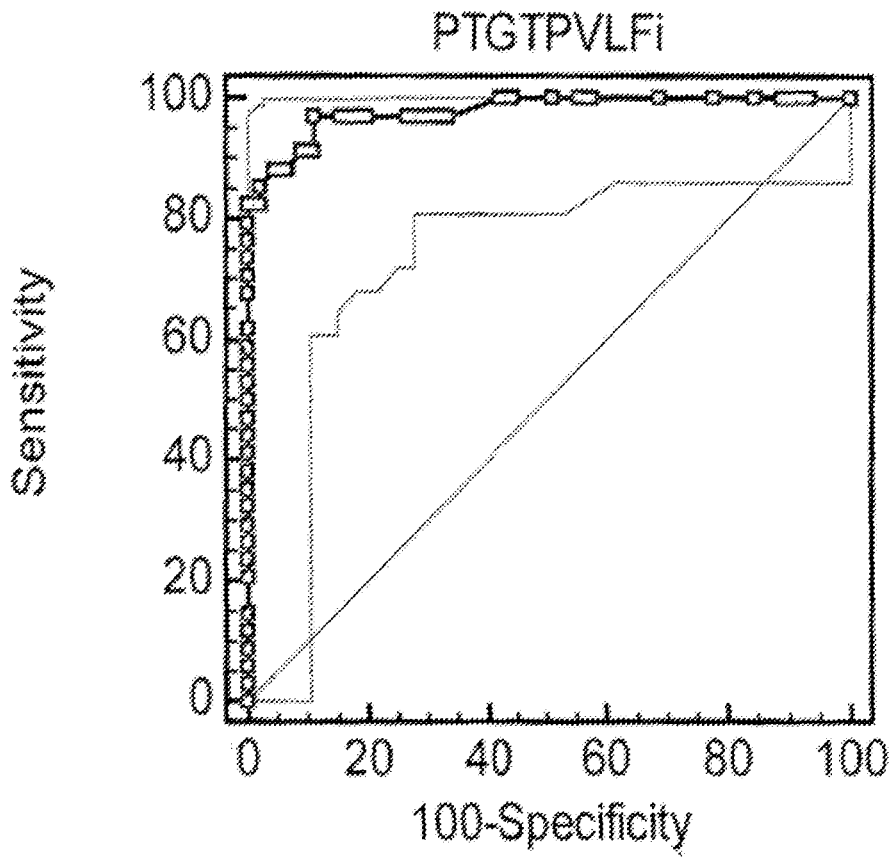
Figure 5:
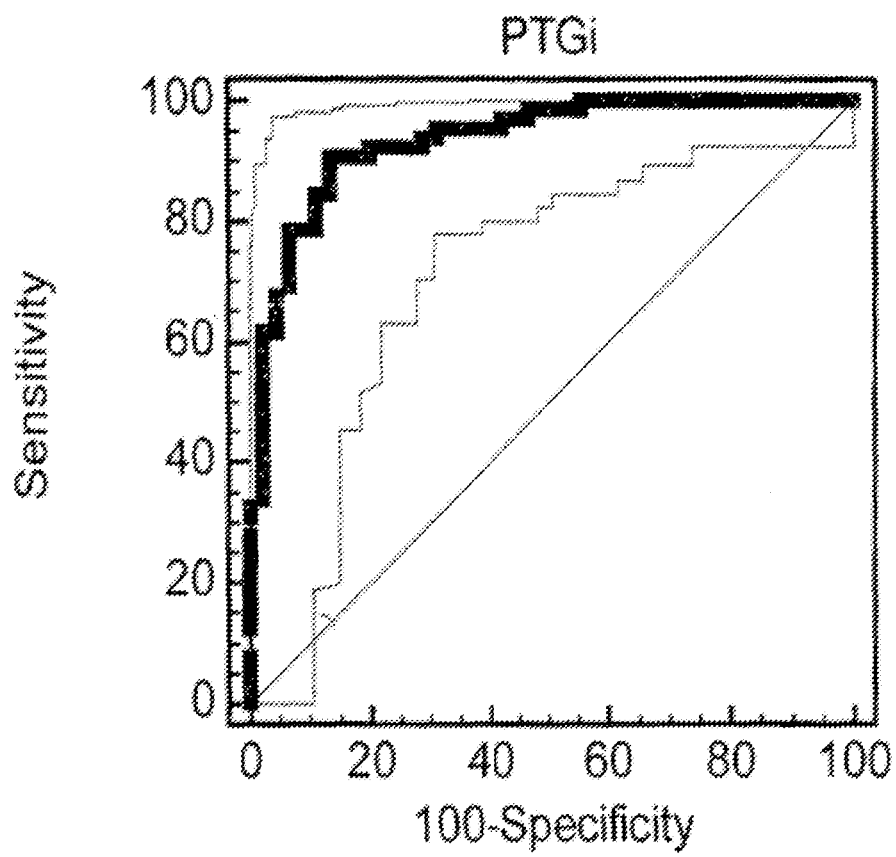

FIG. 4A illustrates the specificity and specificity of PTG TP to detect insulin resistance M value <4.5 (P.0.0001). M value <4.5 (P.0.0001). FIG. 4B illustrates the specificity and sensitivity of PTGVLFi to detect diabetes (P.0.001). FIG. 5 illustrates the specificity and sensitivity of PTGi to detect atherosclerosis (P.0.001).

The studies described below utilized a pulse oximeter system which was used to measure a new parameter calculated with the Fast Fourier Transforms of the oximeter wave form (plethysmograph). Said system uses an oximeter and blood pressure device powered by the USB port of a computing device. The oximeter placed on the index finger of an individual has the ability to display in real time the photoelectrical plethysmography that represents the arterial blood volume changes during the cardiac cycle. Signal processing analysis of the waveform allows determination of the heart rate, the heart rate variability analysis and stiffness or aging index that is inversely proportional to the arterial compliance.

The spectral analysis using the Fast Fourier Transformation (FFT) of the first derivative of total records of the plethysmograph provides 3 frequencies; high, low and very low frequencies, the sum of the 3 frequencies is the PTG TP.

A first study examined Insulin resistance detection using spectral analysis of arterial plethysmography versus Euglycemic Hyperinsulinemic Clamp. This was carried out by Aglecio L. Souza and others at UNICAMP University Campinas Brazil.

The method used was the following. Thirty patients (23 women) in general good health of mean age 32 (range 22-55) years and BMI of 27.3 (range 19-49) Kg·m2, who were candidates for insulin resistance test were included in the study, and underwent hyperinsulinemic euglycemic clamp (HE clamp) test and examination with the TM-Oxi system (a known pulse oximeter system). The TM-Oxi system uses an automatic blood pressure device and an oximeter managed by software, but in this study with focus on signal processing analysis of the oximeter data in spectral analysis. The team investigated the cross-sectional association between insulin resistance (M value, assessed using (HE clamp) and the spectral analysis of the total records of the PTG.

Statistical analysis was performed to correlate M value and PTG TP using Brand Altman Plot. Receiver-operating characteristic curves were also constructed to determine the specificity and sensitivity of PTG TP, Body Mass Index (BMI) and blood glucose in detecting M value <4.5.

The results were as follows. The Spearman's coefficient of rank correlation (rho) was −0.624 (P.0.001). PTG TP had a sensitivity of 90% and specificity of 90% (cutoff #370 m/s2) Area under the Roc curve (AUC)=0.95 to detect M value <4.5 (P.O.OOO1). BMI had a sensitivity of 80% and specificity of 60% (cutoff #28.8 Kgm2) AUC=0.752 to detect M value <4.5 (P.O.O1.). Blood glucose had a sensitivity of 60% and specificity of 95% (cutoff #89.4) AUC=0.810 to detect M value <4.5 (P.0.001).

The conclusion was as follows. PTG TP parameter has the best AUC (0.95) comparing with the other existing available tests to detect the M value <4.5 of the HE clamp. Therefore, PTG TP provided by the TM-Oxi system represents a novel parameter of screening and follow ups for insulin resistance on large scale population. This parameter is independent factor of risk for T2DM and cardiovascular diseases. Such a tool, which is easy to use, non-invasive, and cost-effective, would be of great benefit for the control of pandemic diabetes diseases and its complications. A new study is underway to confirm the results with 100 patients.

A second study looked at a new approach in treatment management and early detection of foot neuropathy in diabetic population and was carried out by Pratiksha G Gandhi and others in Mumbai, India. The background of the study was as follows. The new ADA and ESDA guidelines show the complexity of diabetes treatment, and also the prevention of diabetes complications. The ACCORD study suggests that tight control using AIC <=6.5% actually increases the risk for cardiovascular mortality associated with hypoglycemia.

Therefore, the new recommended 1 AC level was increased to 7%, and the algorithm treatments based only on 1 AC are considered controversial. In this context, new markers in adjunct of AIC in diabetes treatment management and early detection of complications will be useful.

One hundred sixty four patients were included in the study. The patients were separated in 6 groups: Group 1: One hundred two patients (70 males), with the mean age of 56 years (range 26-90), BMI 29 who were diagnosed with diabetes and undergoing treatment (Group 1); Group 2: a subgroup of the Group 1 comprising twenty five patients (26 males) with the mean age of 66 years (range 56-88) who were diagnosed with diabetes undergoing a treatment and signs and symptoms of tingling, burning or electric like pain or Extreme sensitivity to touch in feet; Group 3: a subgroup of the Group 1 comprising sixty eight patients (42 males) with the mean age of 45 years (range 25-85) who were diagnosed with diabetes undergoing a treatment and without signs or symptoms of feet neuropathy; Group 4: a subgroup of the Group 1 comprising thirty one patients (23 males) with the mean age of 65 years (range 47-90) who were diagnosed with diabetes undergoing a treatment and with signs or symptoms of autonomic neuropathy such as muscle weakness or fatigue or Heat or exercise intolerance or bowel, bladder or digestive problems or changes in blood pressure, causing dizziness or lightheadedness; Group 5: a subgroup of the Group 1 comprising 71 patients (49 males) with the mean age of 56 years (range 26-85) who were diagnosed with diabetes undergoing a treatment and without signs or symptoms of autonomic neuropathy; Group 6: Sixty two patients with the mean age of 40 years (range 22-85) who are in good condition without diabetes detected or signs of symptoms of foot neuropathy or autonomic neuropathy.

All the group patients underwent physical examination, questionnaire about know diseases, current treatment, history and symptoms according to the Michigan Neuropathy assessment and exam with the TM-0 xi system and SudoPath system (a galvanic skin response device system). The TM-Oxi system provides a scoring card for cardiometabolic risk factors (CMR Score), autonomic neuropathy risk (ANR Score), Endothelial dysfunction (EndoT Score) and also frequencies of spectral analysis oximeter waveform (photoplethysmography or PTG frequencies).

The SudoPath system uses a galvanic skin response technology in assessing the sudomotor function with a specific measurement process. It allows detection of skin microcirculation disorders, sweat glands density, and Latency of the response. The system provides a sudomotor response Score (SMR Score) based on these 3 parameters for early detection of peripheral foot neuropathy.

The study compared:
1. Groups 1 to group 6 using the PTG very low frequency index (PTG VLFi), CMR score and EndoTscore.
2. Groups 2 and 3 using SMR Score
3. Groups 2 and 6 using SMR Score
4. Groups 4 and 5 and using ANR Score
5. Groups 4 and 6; using ANR Score Statistical analysis was performed using Receiver-operating characteristic (ROC) curves to determine:
1. The specificity and sensitivity PTGVLFi and CMR Score as markers of Diabetes and EndoT score as marker of macrocirculation complication in diabetics patients comparing diabetes patients group and healthy subjects.
2. The specificity and sensitivity of SMR Score in detecting early foot neuropathy signs and symptoms comparing diabetes patients groups, and as marker of microcirculation complication in diabetic patients comparing diabetes patients group and healthy subjects.
3. The specificity and sensitivity ANR Score in detecting autonomic neuropathy signs and symptoms comparing diabetes patients groups, and as marker of autonomic nervous system complication in diabetic patients comparing diabetes patients group and healthy subjects.

The results of the study were as follows. Comparing diabetes patients group and healthy subjects, PTGVLFi had a sensitivity of 96% and specificity of 93.6% (cutoff >26) to detect diabetes (P.0.0001). Area under the Roc curve (AUC) =0.989. Comparing diabetes patients group and healthy subjects group, CMR Score had a sensitivity of 91.2% and specificity of 90% (cutoff >4) to detect diabetes (P.0.0001). Area under the Roc curve (AUC)=0.962. Comparing diabetes patients group and healthy subjects group, EndoT Score had a sensitivity of 88.2% and specificity of 88.6% (cutoff >1) to detect diabetes (P.0.0001). Area under the Roc curve (AUC)=0.962. Comparing diabetes patients group with symptoms of foot neuropathy and diabetes patients group without symptoms of foot neuropathy, SMR Score had a sensitivity of 91.4% and specificity of 79.1% (cutoff >3) to detect foot neuropathy symptoms in diabetic patients (P.0.0001). Area under the Roc curve (AUC)=0.858.

Comparing diabetes patients group with symptoms of foot neuropathy and healthy subjects group, SMR Score had a sensitivity of 91.4% and specificity of 96.8% (cutoff >3) to detect foot neuropathy symptoms in healthy subject (P.0.0001). Area under the Roc curve (AUC)=0.982. Comparing diabetes patients group with symptoms of autonomic neuropathy and diabetes patients group without symptoms of autonomic neuropathy, ANR Score had a sensitivity of 69.4% and specificity of 86.3% (cutoff #>7) to detect autonomic neuropathy in diabetic patients (P.0.0001). Area under the Roc curve (AUC)=0.831. Comparing diabetes patients group with symptoms of foot neuropathy and healthy subjects group, ANR Score had a sensitivity of 87.2% and specificity of 95.1% (cutoff #>5) to detect autonomic neuropathy in healthy subjects (P.0.0001). Area under the Roc curve (AUC)=0.964

The conclusion of the study is as follows. PTGVLFi and CMR Scores provided by the TM-Oxi system have very high sensitivity and specificity to detect diabetes and should be used as new markers in screening and treatment management of diabetic patients. Comparing Diabetes patients and healthy subjects, SMR score, ANR Score and EndoTscore have a high sensitivity and specificity to detect diabetes complications such as respectively foot neuropathy symptoms, autonomic neuropathy symptoms and endothelial dysfunction. Comparing the diabetes patients with and without foot pains or autonomic neuropathy symptoms, SMR score and ANR score will be useful in early detection of such complications in diabetes patients.

In conclusion, on the one hand these results will be a useful tool to assess the susceptibility of patients with risk factors, and will also ensure better monitoring of diabetes treatment in adjunct of AIC percent, and in second hand to assess the susceptibility of patients with risk factors of diabetes complications, thus reducing their occurrence in the long term. But these findings must be confirmed by large scale studies using TM-Oxi and SudoPath system.

A third study related to spectral analysis of photoplethysmography in screening of atherosclerosis and was carried out by Dr Pratiksha G Gandhi, Cardiologist in Mumbai, India. The background of the study was as follows. Atherosclerosis is a leading cause of cardiovascular death due to the increasing prevalence of the disease and the impact of risk factors such as diabetes, obesity or smoking. Sudden cardiac death is the primary consequence of coronary artery disease in 50% of men and 64% of women. Currently the only available strategy to reduce mortality in the at-risk population is primary prevention; the target population must receive screening for atherosclerosis. The value of screening for subclinical atherosclerosis is still relevant, and it has become standard clinical practice with the emergence of noninvasive techniques (radio frequency, measurement of intima-media thickness, and flow-mediated vasodilatation). In this study we present a new non-invasive technique based upon the spectral analysis of the plethysmography provided by an oximeter.

Sixty-three patients (12 women), with the mean age of 62.9 years (range 40-80) who were diagnosed with atherosclerosis using CAG report (Group 1) and forty-seven subjects (13 women) with the mean age of 45, 1 years (range 25-85) who are supposed healthy (group 2), were included in the study. The group 1 was separated into 2 subgroups: Subgroup 1 A: Atherosclerosis patients without surgery such as coronary artery bypass grafting (CABG) or Coronary angioplasty also called percutaneous coronary intervention (PCI); Subgroup IB: Atherosclerosis patients with surgery (CABG or PCI).

These patients and subjects underwent examination with the TM-Oxi system. The TM-Oxi system uses a blood pressure device and oximeter, and the focus of this study was on the signal processing analysis of the oximeter waveform (Photoplethysmography or PTG) and a scorecard based on this analysis (EndoT Score). The study compared the 2 Groups 1 and 2 using the PTG spectral analysis Index (PTGi) and the EndoT Score. The study compared also the 2 subgroups 1 A and IB using the PTG very low frequency (PTG VLF).

Statistical analysis was performed using Receiver-operating characteristic curves (ROC) to determine: the specificity and sensitivity of PTGi and EndoTscore in detecting atherosclerosis comparing group 1 and group 2, and; the specificity and sensitivity of PTGVLF in detecting atherosclerosis patients undergoing in Surgery comparing the subgroup 1 A and IB.

The results were as follows. PTGi had a sensitivity of 86.1% and specificity of 87.3% (cutoff #<40.8) to detect atherosclerosis (P.0.0001). Area under the Roc curve (AUC)

=0.926. EndoTscore had similar results with sensitivity of 86.2% and specificity of 88.2% (cutoff >1) to detect atherosclerosis (P.0.0001). Area under the Roc curve (AUC) =0.902. PTGVLF had a sensitivity of 82.6% and specificity of 100% (cutoff #<69) to detect atherosclerosis patient undergoing in Surgery such as CABG or PCI (P.0.0001). Area under the Roc curve (AUC)=0.952

The conclusion is as follows. PTGi parameter and EndoT Score have high sensitivity and specificity to detect atherosclerosis and will be useful as new markers of the endothelial dysfunction. PTG VLF has a good sensitivity and remarkable 100% of specificity to detect the benefits of coronary surgery. TM-Oxi parameter and Score will be a useful tool to assess the susceptibility of patients with risk factors, and ensures better monitoring of atherosclerosis and surgery, thus reducing the occurrence of cardiovascular events in the long term.

A fourth study involved a cross-sectional assessment to detect Type 2 Diabetes with endothelial and autonomic nervous system markers using a novel system. The background was as follows. Type 2 diabetes mellitus is frequently unrecognized until complications appear. Diabetic autonomic neuropathy is one of the early complications of type 2 diabetes mellitus, resulting in autonomic nervous system (ANS) dysfunction. The purpose of this study was to determine the validity of ANS function indicators to screen for type 2 diabetes mellitus, as measured by the TM-Oxi and SudoPath system.

All enrolled participants completed a basic sociodemographic and medical history questionnaire including current medications. Healthy controls (n=25) underwent a 2-hour oral glucose tolerance test (OGTT) to evaluate glucose, insulin, and insulin C-peptide. Patients with type 2 diabetes mellitus (n=24) were assessed with fasting plasma glucose (FPG) and glycosylated hemoglobin. The TM-Oxi and SudoPath system evaluation was completed by all subjects. Data were analyzed using SPSS 22. Frequency and descriptive statistics were calculated on all variables. The criterion for statistical significance was $\alpha=0.05$.

The results were as follows. The twenty-five healthy controls had a mean age of 37.0 years. The twenty-four type 2 diabetes mellitus patients currently undergoing standard treatment had a mean age of 48.9 years. Based on the American Diabetes Association guidelines, we detected prediabetes in 4 subjects and diabetes in 1 subject, while all other subjects had normal FPG values. At 120 minutes, the correlations between the OGTT and cardiometabolic risk score (CMRS) were: r=0.56 (p=0.004) for glucose and r=0.53 (p=0.006) for insulin.

At 120 minutes, the correlations between the OGTT and photoplethysmography index (PTGi) were: r=−0.56 (p=0.003) for glucose and r=−0.41 (p=0.04) for insulin. The CMRS, PTGi, and plethysmography total power index (PTGVLFi) differed significantly between the diabetes patients and healthy participants. The specificity and sensitivity for the CMRS, PTGi, and PTGVLFi comparing the diabetes patients with healthy controls were high.

The conclusion of the study was as follows. The TM-Oxi and SudoPath system shows promise as a valid, convenient, and non-invasive screening method for type 2 diabetes mellitus. The ANS function and CMR indicators measured by this system may be useful in guiding diabetes and cardiovascular health screening, treatment, and monitoring.

A fifth study involved a spectral analysis of the photoplethysmography to evaluate an independent cardiovascular risk. The background of the study was as follows. The study evaluated homeostatic markers correlated to autonomic nervous and endothelial functions in a population of coronary artery disease (CAD) patients versus a control group. Since CAD is the highest risk marker for sudden cardiac death, the study objective is to determine whether an independent cardiovascular risk score based on these markers can be used alongside known conventional cardiovascular risk markers to strengthen the understanding of a patient's vascular state.

Sixty-five subjects (13 women) with a mean age of 62.9 years (range 40-80 years) who were diagnosed with CAD using coronary angiography (group 1) and seventy-two subjects (29 women) with a mean age of 45.1 years (range 18-85 years) who claimed they were healthy (group 2) were included in the study. These subjects underwent examination with the TM-Oxi and SudoPath systems at IPC Heart Care Centers in Mumbai, India. The TM-Oxi system takes measurements from a blood pressure device and a pulse oximeter. The SudoPath measures galvanic skin response to assess the sudomotor pathway function. Spectral analysis of the photoplethysmograph (PTG) waveform and electrochemical galvanic skin response allow the TM-Oxi and SudoPath systems to calculate several homeostatic markers, such as the PTG index (PTGi), PTG very low frequency index (PTGVLFi), and PTG ratio (PTGr). The focus of this study was to evaluate these markers (PTGi, PTGVLFi, and PTGr) in CAD patients against a control group, and to calculate an independent cardiovascular risk factor score: the PTG cardiovascular disease risk score (PTG CVD), calculated solely from these markers. We compared PTGi, PTGVLFi, PTGr, and PTG CVD scores between the CAD patient group and the healthy control group. Statistical analyses were performed using receiver operating characteristic curves to determine the specificity and sensitivity of the markers to detect CAD at optimal cutoff values for PTGi, PTGVLFi, PTGr, and PTG CVD. In addition, correlation analyses between these markers and conventional autonomic nervous system and endothelial function markers were performed to understand the possible underlying physiological sources of the differences observed in marker values between CAD patients and healthy control patients. Additionally, t-tests were performed between two subgroups of the CAD patient group to determine whether diabetic or coronary artery bypass grafting (CABG) patients have significantly different PTGi marker values.

The results of the study were as follows. Each spectral analysis PTG marker yielded a high specificity and sensitivity to detect CAD. Most notably, the PTG CVD score had a sensitivity of 82.5% and specificity of 96.8%, at a cutoff of 2, when used to detect CAD (P=0.0001; area under the receiver operating characteristic curve=0.967). The PTG spectral analysis markers were well-correlated to other autonomic nervous system and endothelial function markers. CAD diabetic patients (n=27) had a lower PTGi value compared with the CAD non-diabetic patients (n=38): and patients that underwent CABG (n=18) had a higher PTGi value compared with the CAD without CABG surgery patients (n=47).

The conclusion of the study was as follows. The spectral analysis of the photoplethysmography method is noninvasive, fast, operator-independent, and cost-effective, as only an oximeter and galvanic skin response device are required in order to assess in a single testing the autonomic nervous system and endothelial function. The spectral analysis techniques used on the photoplethysmogram, as outlined in this study, could be useful when used alongside conventional known cardiovascular disease risk markers.

Figure 6:
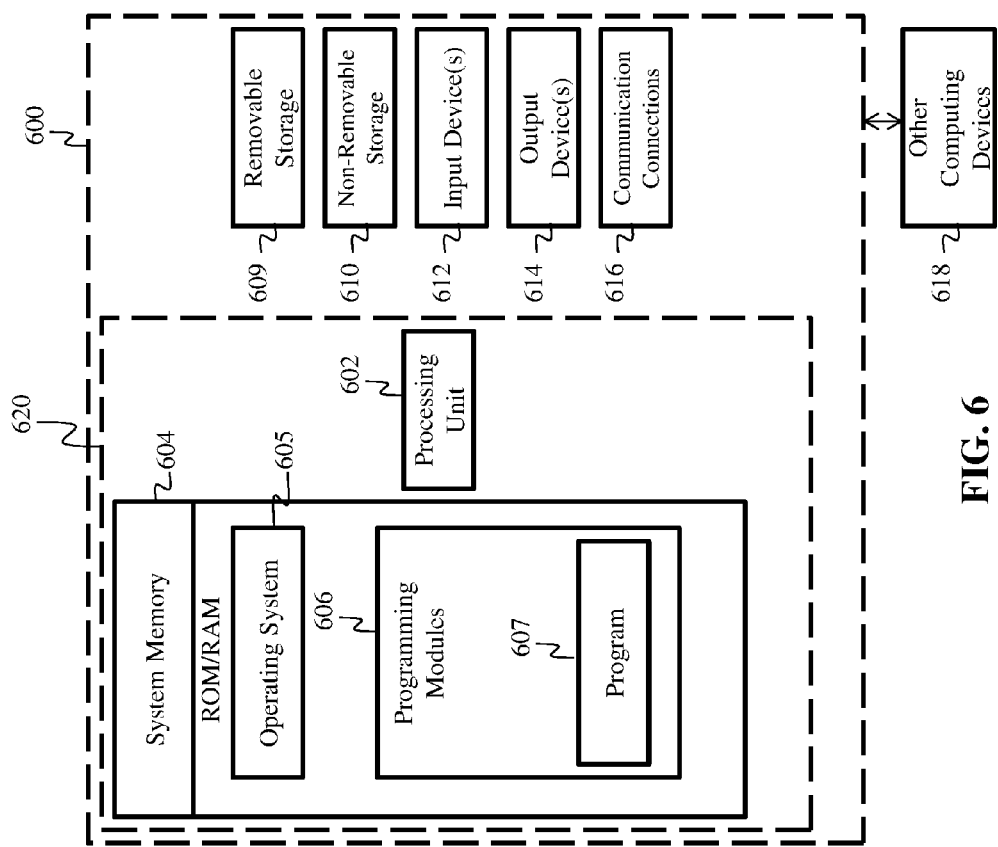
FIG. 6 is a block diagram of a system including a computing device, according to an example embodiment.

FIG. 6 is a block diagram of a system including an example computing device 600 and other computing devices. Consistent with the embodiments described herein, the aforementioned actions performed by servers 102, 112, 140 may be implemented in a computing device, such as the computing device 600 of FIG. 6. Any suitable combination of hardware, software, or firmware may be used to implement the computing device 600. The aforementioned system, device, and processors are examples and other systems, devices, and processors may comprise the aforementioned computing device. Furthermore, computing device 600 may comprise an operating environment for method 300 as described above. Method 300 may operate in other environments and is not limited to computing device 600.

With reference to FIG. 6, a system consistent with an embodiment may include a plurality of computing devices, such as computing device 600. In a basic configuration, computing device 600 may include at least one processing unit 602 and a system memory 604. Depending on the configuration and type of computing device, system memory 604 may comprise, but is not limited to, volatile (e.g. random access memory (RAM)), non-volatile (e.g. read-only memory (ROM)), flash memory, or any combination or memory. System memory 604 may include operating system 605, and one or more programming modules 606. Operating system 605, for example, may be suitable for controlling computing device 600's operation. In one embodiment, programming modules 606 may include, for example, a program module 607 for executing the actions of 102, 112, and 140. Furthermore, embodiments may be practiced in conjunction with a graphics library, other operating systems, or any other application program and is not limited to any particular application or system. This basic configuration is illustrated in FIG. 6 by those components within a dashed line 620.

Computing device 600 may have additional features or functionality. For example, computing device 600 may also include additional data storage devices (removable and/or non-removable) such as, for example, magnetic disks, optical disks, or tape. Such additional storage is illustrated in FIG. 6 by a removable storage 609 and a non-removable storage 610. Computer storage media may include volatile and nonvolatile, removable and non-removable media implemented in any method or technology for storage of information, such as computer readable instructions, data structures, program modules, or other data. System memory 604, removable storage 609, and non-removable storage 610 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 600. Any such computer storage media may be part of device 600. Computing device 600 may also have input device(s) 612 such as a keyboard, a mouse, a pen, a sound input device, a camera, a touch input device, etc. Output device(s) 614 such as a display, speakers, a printer, etc. may also be included. The aforementioned devices are only examples, and other devices may be added or substituted.

Computing device 600 may also contain a communication connection 616 that may allow device 600 to communicate with other computing devices 618, such as over a network in a distributed computing environment, for example, an intranet or the Internet. Communication connection 616 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 604, including operating system 605. While executing on processing unit 602, programming modules 606 (e.g. program module 607) may perform processes including, for example, one or more of method 400's stages as described above. The aforementioned processes are examples, and processing unit 602 may perform other processes. Other programming modules that may be used in accordance with embodiments may include electronic mail and contacts applications, word processing applications, spreadsheet applications, database applications, slide presentation applications, drawing or computer-aided application programs, etc.

Generally, consistent with the embodiments, program modules may include routines, programs, components, data structures, and other types of structures that may perform particular tasks or that may implement particular abstract data types. Moreover, embodiments may be practiced with other computer system configurations, including hand-held devices, multiprocessor systems, microprocessor-based or programmable consumer electronics, minicomputers, mainframe computers, and the like. Embodiments may also be practiced in distributed computing environments where tasks are performed by remote processing devices that are linked through a communications network. In a distributed computing environment, program modules may be located in both local and remote memory storage devices.

Furthermore, embodiments may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments may also be practiced using other technologies capable of performing logical operations such as, for example, AND, OR, and NOT, including but not limited to mechanical, optical, fluidic, and quantum technologies. In addition, embodiments may be practiced within a general purpose computer or in any other circuits or systems.

Embodiments, for example, are described above with reference to block diagrams and/or operational illustrations of methods, systems, and computer program products according to said embodiments. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments have been described, other embodiments may exist. Furthermore, although embodiments have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the claimed subject matter.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for detecting insulin resistance, diabetes, cardiovascular disease and/or autonomic neuropathy in a patient, the system comprising:
   one or more sensors coupled with the patient, the sensors configured for measuring a photoplethysmogram (PTG) and galvanic skin response from the patient;
   a processor communicatively coupled with the one or more sensors, the processor configured for:
      a) executing a spectral analysis on the PTG using Fast Fourier Transform, thereby generating three constituent frequencies: PTG high frequency (PTGHF), PTG low frequency (PTGLF) and PTG very low frequency (PTGVLF) based on the PTG;
      b) calculating PTG Total Power (PTGTP) as the sum of PTGHF, PTGLF, and PTGVLF;
      c) calculating PTG index (PTGi) of the spectral analysis as a sum of amplitudes of the PTGHF, PTGLF, and PTGVLF;
      d) calculating PTG VLF index (PTGVLFi) of the spectral analysis as PTGVLF divided by a value derived from the galvanic skin response;
      e) calculating PTG ratio (PTGr) of the spectral analysis as PTGVLF divided by PTGi;
      f) comparing the PTGi, PTGVLFi, and PTGr of the patient to stored clinical data;
      g) calculating a PTG cardiovascular risk score based on the comparison of the PTGi, PTGVLFi, and PTGr of the patient to the stored clinical data; and
      h) comparing PTGTP, PTGi and PTGVLFi to predefined values that correspond to certain diseases, including insulin resistance, diabetes, cardiovascular disease and autonomic neuropathy; and
   a display for displaying the PTG cardiovascular risk score and said certain diseases that correspond to predefined values that match the PTGTP and PTGi and PTGVLFi.

2. The system of claim 1, wherein the stored clinical data is received via a communications network communicatively coupled with the processor.

3. The system of claim 2, wherein the one or more sensors includes a pulse oximeter for measuring a PTG.

4. The system of claim 3, wherein the one or more sensors includes a galvanic skin response device for measuring galvanic skin response.

5. The system of claim 2, wherein the predefined values that correspond to certain diseases are received via the communications network.

6. The system of claim 5, wherein the one or more sensors includes a pulse oximeter for measuring a PTG.

7. The system of claim 6, wherein the one or more sensors includes a galvanic skin response device for measuring galvanic skin response.

8. The system of claim 7, wherein the step of comparing PTGTP, PTGi and PTGVLFi to predefined values comprises determining whether PTGTP is greater than a predefined value of 370 $ms^2$, and if so, said PTGTP corresponds to insulin resistance.

9. The system of claim 8, wherein the step of comparing PTGTP, PTGi and PTGVLFi to predefined values comprises determining whether PTGi is lower than a predefined value of 40, and if so, said PTGi corresponds to diabetes with high risk of cardiovascular disease.

10. The system of claim 9, wherein the step of comparing PTGTP, PTGi and PTGVLFi to predefined values comprises determining whether PTGVLFi is greater than a predefined value of 33, and if so, said PTGVLFi corresponds to diabetes with a high risk of autonomic neuropathy.

11. A method for detecting insulin resistance, diabetes, cardiovascular disease and/or autonomic neuropathy in a patient, the method comprising:
   a) receiving, from one or more sensors coupled with the patient, a photoplethysmogram (PTG) and galvanic skin response from the patient;
   b) executing a spectral analysis on the PTG using Fast Fourier Transform, thereby generating three constituent frequencies: PTG high frequency (PTGHF), PTG low frequency (PTGLF) and PTG very low frequency (PTGVLF) based on the PTG;
   c) calculating PTG Total Power (PTGTP) as the sum of PTGHF, PTGLF, and PTGVLF;
   d) calculating PTG index (PTGi) of the spectral analysis as a sum of amplitudes of the PTGHF, PTGLF, and PTGVLF;
   e) calculating PTG VLF index (PTGVLFi) of the spectral analysis as PTGVLF divided by a value derived from the galvanic skin response;
   f) calculating PTG ratio (PTGr) of the spectral analysis as PTGVLF divided by PTGi;
   g) comparing the PTGi, PTGVLFi, and PTGr of the patient to stored clinical data;
   h) calculating a PTG cardiovascular risk score based on the comparison of the PTGi, PTGVLFi, and PTGr of the patient to the stored clinical data;
   i) comparing PTGTP, PTGi and PTGVLFi to predefined values that correspond to certain diseases, including insulin resistance, diabetes, cardiovascular disease and autonomic neuropathy; and
   j) displaying the PTG cardiovascular risk score and said certain diseases that correspond to predefined values that match the PTGTP and PTGi and PTGVLFi.

12. The method of claim 11, wherein the stored clinical data is received via a communications network communicatively coupled with the processor.

13. The method of claim 12, wherein the one or more sensors includes a pulse oximeter for measuring a PTG.

14. The method of claim 13, wherein the one or more sensors includes a galvanic skin response device for measuring galvanic skin response.

15. The method of claim 12, wherein the predefined values that correspond to certain diseases are received via the communications network.

16. The method of claim 15, wherein the one or more sensors includes a pulse oximeter for measuring a PTG.

17. The method of claim 16, wherein the one or more sensors includes a galvanic skin response device for measuring galvanic skin response.

18. The method of claim 17, wherein the step of comparing PTGTP, PTGi and PTGVLFi to predefined values comprises determining whether PTGTP is greater than a predefined value of 370 ms2, and if so, said PTGTP corresponds to insulin resistance.

19. The method of claim 18, wherein the step of comparing PTGTP, PTGi and PTGVLFi to predefined values comprises determining whether PTGi is lower than a predefined value of 40, and if so, said PTGi corresponds to diabetes with high risk of cardiovascular disease.

20. A system for detecting insulin resistance, diabetes, cardiovascular disease and/or autonomic neuropathy in a patient, the system comprising:

one or more sensors coupled with the patient, the sensors configured for measuring a photoplethysmogram (PTG) and galvanic skin response from the patient;

a processor communicatively coupled with the one or more sensors, the processor configured for:
  a) executing a spectral analysis on the PTG using Fast Fourier Transform, thereby generating three constituent frequencies: PTG high frequency (PTGHF), PTG low frequency (PTGLF) and PTG very low frequency (PTGVLF) based on the PTG;
  b) calculating PTG Total Power (PTGTP) as the sum of PTGHF, PTGLF, and PTGVLF;
  c) calculating PTG index (PTGi) of the spectral analysis as a sum of amplitudes of the PTGHF, PTGLF, and PTGVLF;
  d) calculating PTG VLF index (PTGVLFi) of the spectral analysis as PTGVLF divided by a value derived from the galvanic skin response;
  e) calculating PTG ratio (PTGr) of the spectral analysis as PTGVLF divided by PTGi;
  f) comparing the PTGi, PTGVLFi, and PTGr of the patient to stored clinical data, and assigning each of PTGi, PTGVLFi, and PTGr a value indicating a result of said comparing;
  g) calculating a PTG cardiovascular risk score as a sum of the values assigned to each of PTGi, PTGVLFi, and PTGr as a result of said comparing; and
  h) comparing PTGTP, PTGi and PTGVLFi to predefined values that correspond to certain diseases, including insulin resistance, diabetes, cardiovascular disease and autonomic neuropathy; and a display for displaying the PTG cardiovascular risk score and said certain diseases that correspond to predefined values that match the PTGTP and PTGi and PTGVLFi.

* * * * *